United States Patent [19]

Kuznetsov

[11] Patent Number: 5,563,120
[45] Date of Patent: Oct. 8, 1996

[54] CYTOKINE PREPARATION FOR IMMUNOTHERAPY

[75] Inventor: Vladimir P. Kuznetsov, Moscow, Russian Federation

[73] Assignee: Intelcor Biotech Enterprises, Inc., Manitoba, Canada

[21] Appl. No.: 244,401

[22] PCT Filed: Sep. 20, 1993

[86] PCT No.: PCT/CA93/00381

§ 371 Date: Aug. 23, 1994

§ 102(e) Date: Aug. 23, 1994

[87] PCT Pub. No.: WO94/06820

PCT Pub. Date: Mar. 31, 1994

[30] Foreign Application Priority Data

Sep. 22, 1992 [CA] Canada ................................. 2078805

[51] Int. Cl.⁶ ......................... A61K 37/02; A61K 35/16; C12P 21/04; C07K 3/12
[52] U.S. Cl. .............................. 514/2; 424/529; 424/534; 424/530; 435/70.4; 435/70.5; 435/240.2; 435/240.21; 530/350; 530/351; 530/412; 530/415; 530/416; 530/419; 530/421
[58] Field of Search ..................... 435/70.1, 70.3, 435/70.4, 70.5, 240.2, 240.21; 530/412, 417, 350, 351, 415, 416, 419, 421; 514/2; 424/529, 530, 534

[56] References Cited

U.S. PATENT DOCUMENTS 4,696,899 9/1987 Toth et al. ................................. 435/68

OTHER PUBLICATIONS

Kuznetsov et al, 'The Complex Preparation of Ifn–Alpha and Cytokines–Leukinferon for Injections (LF): Immunobiological Properties, Clinical Effectiveness' (Abstract), Journal of Interferon Research, vol. 10, No. S1, Nov. 1990, New York, USA p. S175.

Botsvadze et al, 'Treat Acute Hepata Consist Course Specified Medicine Preparation Prescribed Manner Increase Efficiency', Database WPI, Week 9245 Derwent Publications Ltd., London, Great Britain, Dec. 1991 (Abstract).

Horowitz, B., Methods in Enzymology, ed. Pestka, vol. 119, Academic Press, Inc., N.Y. 1986, pp. 39–47.

*Primary Examiner*—David M. Naff
*Attorney, Agent, or Firm*—Weiser & Associates, P.C.

[57] ABSTRACT

A cytokine composition is prepared for use in immunotherapy of various diseases. The composition is prepared by culturing leucocytes previously infected with a virus in a culture medium containing a transal composition isolated from plasma and a complex of proteinase inhibitors composition isolated from plasma, separating leucocytes from the medium, removing impurities from the medium, and recovering a cytokine composition containing the transal composition and the complex of protease inhibitors composition. The transal composition contains transferrin, albumin and a 40 kDa protein and the complex of protease inhibitors composition contains $\alpha_2$-macroglobulin, a 160 kDa protein, an 80–60 kDa protein and a 20 kDa protein. The transal composition is prepared by mixing plasma with chloroform and recovering an aqueous phase, precipitating gamma globulins from the aqueous phase with polyethylene glycol to recover another aqueous phase, passing this aqueous phase through an anion exchange column and recovering proteins that bind to the column. The complex of protease inhibitors composition is prepared using steps for preparing the transal composition except that additional steps are used of collecting eluate from the anion exchange column, passing the eluate through a $Cu^{++}$ chelate anion exchange column and recovering proteins that bind to the column.

18 Claims, No Drawings

CYTOKINE PREPARATION FOR IMMUNOTHERAPY

FIELD OF THE INVENTION

The present invention relates to a novel cytokine composition, a method for its preparation, and the use of the preparation in the immunotherapy of various diseases such as bacterial infections, viral infections and cancers.

BACKGROUND OF THE INVENTION

The immune system provides defence for the body against infectious agents such as bacteria, viruses, fungi and parasites. More recently, it has been shown that the state of the immune system can be linked to the susceptibility to developing certain types of cancers. For example, it has been shown that in certain immune deficient states, most notably Acquired Immune Deficiency Syndrome (AIDS), the incidence of cancer is greatly increased. Immunotherapy has become an important therapy against various infectious agents and even in the treatment of cancer. One branch of immunotherapy involves using immunomodulating agents that can modulate, induce or increase the immune response.

One group of immunomodulating agents that has been extensively studied includes the cytokines. Cytokines are the chemical messengers of the immune system and are produced by immune cells such as lymphocytes and monocytes. One cytokine, namely interferon (IFN), has been shown not only to induce the immune system but also to act directly on tumors to inhibit proliferation of the tumor cells. Interferon is well known in the art. Details on its characterization as well as methods for its preparation can be found in Methods in Enzymology, Volume 119, "Interferons, PART C" 1986.

Although both crude as well as purified preparations of cytokines, such as interferon, are currently available, the problems with these known preparations include the following. Crude preparations generally contain proteinases which break down the cytokines and thereby decrease the stability of the preparation. Proteinase inhibitors are available but these are generally toxic or antigenic to man and thus are not useful in therapeutic applications. On the other hand, while purified interferon is generally proteinase free, the methods for purifying interferon known to date generally result in a poor yield of interferon. Furthermore, the biological activity of a purified preparation is generally lower than that of a crude interferon preparation.

Early in the 80s, it was observed that a crude preparation of interferon activated human natural killer cells (NK) more effectively than purified IFN prepared from the same batch of crude IFN. As shown in Table A the highest degree of NK activation can be achieved with a crude IFN titer of 50 IU/ml and a purified IFN titer of 625 IU/ml. These titers resulted in activation of the NK cells of 550% and 600%, respectively. From this data it was concluded that crude IFN has a higher potential of immunoactivation which is likely due to the presence of some other cytokines together with IFN.

It was later found that mixed cultures of donor Leukocytes produced (in response to viral induction and interaction of cells with different genotypes) cytokines as such as Interleukin-1 (IL-1), Tumor Necrosis Factor (TNF), Migration Inhibition Factor (MIF), Leucocyte Migration Inhibition Factor (LIF), together with IFN-α. It is known that these cytokines participate in the activation of immune effector cells (mainly macrophages, $T_4$-lymphocytes, neutrophils) and participate in the immune recognition of antigen and its elimination from the body. These reactions present the first stage of the immune response manifested by effectors in response to an antigen encounter. Amplification of immune response, developing specific humoral reactions and memory cells are events that occur later and depend on effective immune reactions in the first (non-specific) stage of immune response.

The cytokines such as IFN, IL-1, TNF, MIF and LIF, have different physico-chemical properties, therefore it is very difficult to retain composition that is active and composed of a mixture of the cytokines preparation after chemical purification procedures. Furthermore, for medical preparations containing protein it is very important to limit the quantity of total protein because foreign proteins (especially when used by parenteral routes) can induce sensitization. However, lowering of the level of protein increases the sensitivity of the active factors to proteolysis. As a result, the activity of such preparations after technological procedures is-decreased and problems with storage of the drug forms appear.

Therefore, in view of all of the above it is desirable to produce a cytokine composition that includes a mixture of cytokines and that is largely substantially free of proteinases while at the same time showing good biological activity.

SUMMARY OF THE INVENTION

The present invention relates to a novel cytokine composition (which has been termed leukinferon) as well as a method for its preparation and its use in the immunotherapy of various conditions. The cytokine composition is produced by virally induced donor leucocytes. The cytokine composition comprises human leukocyte interferon IFN-α as well as other cytokines of the first, non-specific, phase of the immune response (I1-1, TNF, MIF, LIF, etc.) in their naturally occurring ratio.

The novel methods according to the present invention produce a cytokine composition that avoids the drawbacks of the prior art. One novel ingredient of the cytokine composition is a complex of proteinase inhibitors (CPI), that has previously been isolated from donor plasma. CPI inhibits proteolysis reactions in cytokine preparations. Furthermore, since CPI is naturally occurring and isolated from humans, it is non-toxic to humans.

A second ingredient, a novel protein composition, which has been termed transal, is also added during the preparation of the cytokine composition according to the present invention. Transal is a naturally occurring group of proteins that is isolated from donor plasma. After the addition of transal and CPI, the culture medium containing the cytokines is further treated to remove impurities such as human viruses, antigens and antibiotics or other low molecular weight components.

Accordingly, the present invention provides a method of producing transal comprising the steps of:

a) mixing plasma with chloroform, b) recovering a first aqueous phase, c) precipitating gamma globulins from the first aqueous phase;

d) recovering a second aqueous phase;

e) passing the second aqueous phase through an ion exchange column, f) recovering proteins that bind to the column.

The present invention also provides a transal composition comprising transferrin, albumin and a 40 kDa protein.

The present invention further provides a method of producing a complex of proteinase inhibitors comprising the steps of:

a) mixing plasma with chloroform, b) recovering a first aqueous phase, c) precipitating gamma globulins from the first aqueous phase;

d) recovering a second aqueous phase;

e) passing the second aqueous phase through an ion exchange column, f) collecting an eluate that passes freely through the column, g) passing said eluate through a $Cu^{++}$ chelate column, h) recovering proteins that bind to the column.

The present invention further provides a complex of proteinase inhibitors composition comprising $\alpha_2$-macroglobulin, a 160 kDa protein, an 80–60 kDa protein and a 20 kDa protein.

The present invention also provides a process for the production of a cytokine composition comprising the steps of;

a) culturing virally-induced leucocytes with transal and complex of proteinase inhibitors in liquid culture medium;

b) removing the leucocytes from the liquid; and c) treating the liquid to remove impurities.

The leukinferon composition has been shown to be effective in the treatment of a variety of disease conditions such as bacterial infections, viral infections, as well as certain types of cancer.

DETAILED DESCRIPTION OF THE INVENTION

1. Method of Preparation of Transal 0.5 L of donor plasma is freshly collected, anticoagulant is added, and the plasma is cooled to 6°±2° C. Chloroform is added (10% volume/volume) and the mixture is agitated for 30 minutes and then allowed to stand for another 10 to 15 minutes to allow the upper aqueous and the lower chloroform layers to separate. The aqueous layer is removed and centrifuged at 2,000 x g, for 20 minutes at 6°±2° C. The supernatant is removed and adjusted to pH 8.5 with 0.02M NaOH. Subsequently, a ⅕ (v/v) solution of 30% polyethylene glycol is added and the mixture is kept at room temperature for 20 minutes. The gamma-globulin fraction precipitates and can be separated by centrifugation at 2,000 x g, 15 min. at 10°±2° C. The resulting supernatant is then passed through a DEAE cellulose column (DEAE-52Servacel, Serva, Germany) which has been equilibrated with 0.01M tris-HCl buffer, pH 8.5 and 0.01M NaCl. The fraction passing freely through the column is collected and used to prepare the complex of proteinase inhibitors (CPI) which will be discussed in more detail below. The column is washed and then the fraction binding to the column (which is a fraction containing the transal) is eluted with 0.01M tris-HCl buffer, pH 8.5 and 0.5M NaCl. The volume of the eluate containing the transal is, generally around 0.25 liters and has a protein concentration of 5 to 15 mg/ml. Polyacrylamide gel electrophoresis of the eluate shows that the main components of the eluate are albumin and transferrin. There is also present a minor protein with a molecular weight of 40 kDa. The entire eluate is termed transal. The eluate is substantially or totally free of gamma globulin. Accordingly, the term "transal" as used herein denotes the product of the above described process which comprises a mixture of transferrin, albumin and a 40 kDa protein.

The eluate is desalted by dialysis against 0.01M Na phosphate buffer, pH 7.2 with 0.15M NaCl (PBS) or by gel filtration through a Sephadex G-25 "coarse" column and sterilized by 0.2 μ membrane filtration.

Table 1 is a comparative study showing the effect of transal, plasmal or native plasma on interferon (IFN) production in a crude interferon preparation. Plasmal is plasma that has been treated to remove gamma globulins. This table shows that with transal, one can use 3.5 times less protein as compared with native plasma, or 2.8 times less protein as compared with plasmal to obtain the same yield of IFN activity. Therefore, this table shows that transal is a very effective component in a cytokine composition.

2. Preparation of the Complex of Proteinase Inhibitors

One of the main problems with crude cytokine preparations is that the proteinase activity is generally high and causes the proteolysis of the cytokines in the composition. Many non-specific and specific inhibitors of proteinases in crude interferon compositions were studied and it was shown that these compositions are generally resistant to such inhibitors. In particular, it was shown that each of dextran, polyglycine, ethylenediaminotetra-acetate, aminocaproic acid, and kontrycal in a concentration of 0.1–1.0 mg/ml had no effect on proteolysis determined by the azacasein test. Soybean trypsin inhibitor at 1 mg/ml reduced proteolysis by one half. Phenylmethylsulfonidefluoride (Serva, Germany), was found to be a highly effective inhibitor. However, it is very toxic which prevents it from being used in medical compositions.

Proteinases are present in extracellular biological fluids and they are common mediators of the acute phase of inflammation. The body also has proteinase inhibitors to control the proteolysis by the proteinase. For example, proteinase inhibitors with wide spectrum inactivation, such as $\alpha_2$-macroglobulin, are present in healthy donor plasma in quite large quantities—up to 3 mg/ml. Therefore, it was desirable to isolate such naturally occurring proteinase inhibitors for use in medical preparations.

The naturally occurring complex of proteinase inhibitors (CPI) was isolated from the fraction freely eluting from the DEAE Sepharose column as described in the preparation of transal in 1) above. The eluate was collected and the pH was adjusted to 6.5 with 0.02M HCl. The eluate was then loaded on to a $Cu^{++}$ chelate Sepharose 4B (Pharmacia, Sweden) column that had previously been equilibrated with 0.02M phosphate buffer, pH 6.5 and 0.8M NaCl. The column was washed several times with a 0.02M phosphate buffer solution at pH 7.4 with 0.08M NaCl. The inhibitors were eluted with 0.1M acetate buffer solution, pH 4.5 and 0.5M NaCl. This eluate contained protein that gave two peaks, the antiproteinase activity being present mainly in the first peak. Material corresponding to the first peak was dialysed against 0.01M phosphate buffer solution, pH 7.2 with 0.15M NaCl. Alternatively, it may be desalted on a Sephadex G-25 column (Pharmacia, Sweden), by adding 0.1M phosphate buffer pH 7.2 with 1.5M HCl at ¹⁄₁₀ of the eluate volume.

Starting from 0.5 liters of donor plasma it is possible to obtain approximately 264±56 ml of the proteinase-containing fraction with an average of 13.26±1.44 ml of total protein. The composition of CPI was analyzed by electrophoresis on polyacrylamide gel. The gel shows that CPI contains 4 fractions. The major protein corresponds to the $\alpha_2$macroglobulin standard. The minor fractions correspond to 160, 80–60 and 20 kDa. Accordingly, the term "complex of proteinase inhibitors" (CPI) as used herein refers to the product of the above described process which comprises a mixture of $\alpha_2$macroglobulin, a 160, an 80–60 and a 20 kDa protein.

The effect of the CPI on proteinase activity is shown in Table 2. The level of proteinase activity is compared to a 0.025% trypsin in solution. As can be seen from this table, a preparation containing only plasmal has as much as 27% of proteinase activity as compared to the standard. However, when using a preparation containing transal (6%) as well as CPI (at 50 mg/ml), no proteinase activity is observed.

3. Preparation of Leukinferon

Leukocytes are isolated from buffy coats collected from healthy donors with the use of erythrocyte precipitants, such as dextran or polyvinyl alcohol and subsequent hemolysis. Leukocytes are cultured at 37.5° C. in culture medium containing insulin, human plasma, heparin and 100 IU/mL human IFN$\alpha$. After 2 hrs incubation the inducer virus—Newcastle disease virus—is added and incubation is continued for 20 min. Induced leukocytes are collected by centrifugation at 600 x g, 20 min, 6°±2° C. and are suspended in culture medium number 199 or minimal Eagles medium without phosphate at a concentration of 6 million cells/ml. A 6% v/v solution of transal as well as 15 mg/ml of CPI and 0.05M sodium succinate is added to the cells which are cultured for another 10 to 14 hours at 37.5° C. The cells are then separated by centrifugation at 600 x g for 20 minutes at 6°±2° C. The resulting supernatant ms further used to prepare the leukinferon.

The supernatant is treated to remove impurities such as human viruses, antigens of virus inducer and chicken allantoic fluid as well as antibiotics and other low molecular weight components of the culture medium. For example, the antigens may be removed by negative immuno-absorption on antibodies which have been obtained from the serum of animals that have previously been immunized with these antigens and then immobilized on a neutral carrier. The human viruses may be inactivated chemically by treatment with hydrogen peroxide in chloroform. The antibiotics and other low molecular weight components may be removed by gel filtration through Sephadex G-25 or ultrafiltration on membranes with an excluding limit of not more than 10 kDa.

In one preferred embodiment, the above described impurities may be removed as follows. The pH of the supernatant is adjusted to 8.0 (0.01NaOH) and NaCl is added as a solid to final concentration 0.5M. Hydrogen peroxide is added to concentration 0.5 % (v/v) and the crude composition is kept at least two days at 6°±2° C. A column (150×26 mm) containing 80 mL of antibodies to viral and allantoic fluid antigens, immobilized on Sepharose 4B, is used for purification of 2.0±0.1 L of crude cytokine composition with a capacity 0.1 L/hr.

Before the column is used it is washed with a solution of 10 µg/µl CPI in 0.01M phosphate buffer pH 8.0 and 0.5M NaCl. CPI is also added to the crude composition to final concentration 50 µg/ml. Then, the crude composition is passed through the column with velocity up to 100 ml/hr.

In the immunoabsorption process the active components of the crude preparation pass freely through the column while the antigenic impurities bind with antibodies and are held by the column. This method (termed negative immunoabsorbtion) allows the composition of all active fractions to remain unchanged.

The fraction passing through the column is collected and treated with chloroform to inactivate viruses. Chloroform is added at a concentration of 10% (v/v). The mixture is kept 30 min at room temperature with agitation. The agitation is stopped for 10 min and the upper layer is collected and centrifuged at 6000 x g, 20 min, 6°±2° C. The lower layer of chloroform extract and precipitate are discarded. The supernatant after centrifugation is desalted by chromatography on a column (60×2800) containing 1.1 kg Sephadex G-25 "coarse" (Pharmacia, Sweden) with velocity up to 0.5 L/hr.

The protein fraction is collected and dialyzed against 0.01M PBS, 0.15M NaCl and 1 mg/ml mannite. The supernatant is then sterilized by filtration on 0.2 µ membrane, dispensed into ampoules and lyophylized for storage.

EXPERIMENTAL DATA

Leukinferon has been tested in numerous in vitro and in vivo clinical studies and has been shown to have very significant immunomodulatory activity as exemplified below.

IN-VITRO STUDIES

EFFECT ON MAJOR HISTOCOMPATIBILITY COMPLEX (MHC) EXPRESSION

It is well known that MHC antigens play a key role in immune responses and they take part directly in the immune recognition of foreign antigen. It is also known that MHC expression is stimulated by IFN-$\gamma$ while IFN-$\alpha$ has little effect, in vitro, on MHC expression.

The effect of leukinferon on the MHC expression of Human Leukocyte Antigen (HLA-DR) on mononuclear cells from donor blood was compared with purified alpha interferon (IFN-$\alpha$) as well as gamma interferon (IFN-$\gamma$). The results are shown in Table 3. As can be seen from Table 3, leukinferon showed an index of amplification of 4.4 compared to 3.1 for gamma interferon and 1.4 for alpha interferon.

B. EFFECT ON HIV INFECTION

Leukinferon was tested for its ability to inhibition infection of MT4 cells by the Human Immunodificiency Virus (HIV), in vitro. The results are summarized in Table 4. As can be seen from this Table, leukinferon at concentrations as low as 5U/ml inhibited the infection of MT4 cells by HIV-1 even after 7 days in culture.

CLINICAL TRIALS

The leukinferon preparation has been tested on a number of patients with bacterial infections, vital infections and cancer. Some of the diseases tested to date are summarized in Table 5.

The results of the clinical studies will be described in detail with regards to four specific examples, namely sepsis, salpingoophorite, hepatitis B and breast cancer.

EXAMPLE 1

Sepsis

Eighteen young children suffering from sepsis caused by gram-negative microorganisms were given 4–6 intramuscular injections of the leukinferon every second day in combination with basic therapy such as antibiotics, analgesics. After treatment, various parameters of immunological function were assayed. The results are shown in Table 6. As can be seen from Table 6, when leukinferon was administered along with the basic therapy, the number of circulating immune complexes (CIC) was reduced, the killing function of neutrophils was restored (as determined by NCT test) as was the number of phagocytic neutrophils. The phagocytic index also was increased when calculated as the number of bacteria ingested. The completeness of phagocytosis also increased.

These results indicate that administration of leukinferon enhance the effectiveness of the immune system. Clinical improvement was also faster with the group treated with leukinferon.

EXAMPLE 2

Salpingoophorite

Salpingoophorite is an inflammation of the tuba uterina caused by a mixed bacterial infection of *E. coli*, Klebsiella, Candida, etc. This condition generally results in infertility. Thirty women suffering from salpingoophorite were given, intramuscularly, one ampoule of leukinferon twice a day for three days and then one ampoule a day for two days. Blood samples were taken before treatment as well as 5 to 7 days thereafter. The results of the effect of leukinferon on the blood cells of the women are shown in Table 7. As can be seen from Table 7, leukinferon therapy has no effect on the levels of immunoglobulin M or G or on the level of circulating C3–C4 components of complement. The number of differentiated B-lymphocytes increased but not significantly. However, the numbers of T-lymphocytes increased significantly as did their functional activity as shown by RBTL on PHA and E-RFC.

Following treatment, the recovery rate was 60% and full restoration of child bearing function was observed in 41% of the women.

EXAMPLE 3

Breast Cancer

Leukinferon was administered by adoptive immunotherapy to women suffering from Stage III Breast Cancer. The women's leukocytes were collected by cytophoresis, incubated with leukinferon and transfused back to the patient. These mononuclear cell populations were assayed following treatment. The results are also shown in Table 8. As can be seen from this Table, leukinferon therapy resulted in an increase in the number of cells expressing MHC, an increase in T-helper, NK and other cytotoxic sub-populations having the markers CD4, CD11ab and CD38. However, the quantity of T-suppressor lymphocytes (CD8, CD22 and CD58) did not change, resulting in an increased ratio of T4/T8 cells. The level of circulating monocytesmyeloid cells (CD15) was slightly reduced.

The women were observed for a period of 2 years and on average cancer was decreased by almost three times.

EXAMPLE 4

Acute Hepatitis B

Leukinferon was administered to patients with acute hepatitis B. The results of this study demonstrated that leukinferon induced the fast reverse development of the main clinical symptoms of infection and intensified the normalization of laboratory data characterized by the liver function. Replication of the hepatitis virus in the body was completely inhibited in most patients. The immunostimulating activity of leukinferon was also observed as the number of T-lymphocytes was increased, natural killer cells were activated, the frequency of sero conversions of surface and internal antigens of the virus were increased. After six months, it appeared the viral surface antigen in patients treated with leukinferon was completely absent as compared to 30% presence in patients that received a placebo.

In summary the above examples illustrate that leukinferon has a positive effect on the immune system which, as illustrated herein and has been shown extensively in the literature, generally results in a positive prognosis for patients suffering from diseases in which the immune system is somehow depressed or is required in order to effectively combat the infection or disease.

Examples of Treatment Protocols

While examples 1–4 illustrate the results of clinical studies done on four specific illnesses, as previously stated, leukinferon has been tested on a wide variety of bacterial and viral infections as well as different forms of cancer. While the treatment regime varies depending on the disease or illness, some guidelines some guidelines are given below regarding the use of interferon in different situations.

Recommended Courses for Bacterial Infections
Prophylaxis

LF is highly effective for prophylaxis against bacterial complications in surgical patients with functional immunodeficiency. For this purpose, LF may be used, via intramuscular (IM) injections, 1–2 times every other day before surgery, on the next day after and then 2–3 injections every other day. Such a regime can reduce the frequency of postsurgical complications and promote the healing processes of the wound.

For prophylaxis of postnatal infections in women following childbirth, LF can be given IM on the day of delivery and 1–2 times every other day thereafter. Indications are inflammatory phenomena in placenta, pyelonephritis and other bacterial diseases.

In serious situations when medical help is not readily available, patients may be given LF IM daily or every other day to prevent bacterial infection.

Therapy

In acute bacterial infections, LF may be given IM daily or every other day (up to 5 injections) at the beginning of the therapy and then 2 times a week until evidence of stabilization of immune status and clinical symptoms disappear.

In the therapy of lung diseases, IM injections may be combined with aerosol inhalations of 1–2 ampoules of LF dissolved in 5–10ml 1–2 times a week.

In patients with purulent peritonitis, including pelvioperitonitis, LF may be given as 3 injections IM every other day and then twice a week. For such patients, an effective combination is IM injections combined with local introduction of 2 ampoules of LF dissolved in 50 ml of saline with antibiotics for treatment of the abdominal cavity.

Patients with pyelonephritis may be given LF, 2–3 I.M. injections every other day and then twice a week for 1–3 weeks.

Viral Infections

For therapy of acute hepatitis B, LF may be injected 1–3 times a day for first 1–3 days (intensity depends on gravity of intoxication phenomena), then every other or third day up to occurrence of stable normalization of liver function and suppression of antigenemia.

In patients with chronic hepatitis B, LF may be give IM 2–3 injections a week.

Patients with influenza or other acute respiratory viral infections, LF may be give via IM injections combined with inhalation of one ampoule, for 3 days by each route.

In therapy of shingles and chicken-pox, it is recommended to use LF daily for 3 days, then every other day. It is useful to apply LF locally by irrigating the oral cavity (one ampoule dissolved in 5–10 ml of saline). The same course is effective in treating viral stomatitis.

Oncological diseases

In patients with basal cell carcinoma, LF may be injected SC 2 times a day in healthy skin bordering the lesions.

To accelerate the healing processes and retard the metastases development in patients with breast cancers and sarcoma, LF may be given 1–3 injections IM before surgery and 1–3 times every day after and then 2 injections a week.

To improve antitumour effectiveness of the therapy it is recommended to combine LF with human leucocyte interferon for injections of $1 \times 10^6$ IU 1–2 times a week.

TABLE A

ACTIVATION OF HUMAN NK BY CRUDE AND PURIFIED IFN PREPARED FROM THE SAME BATCH OF LEUCOCYTES

| Preparations | IFN activity (IU/ml) | NK activation$^x$ |
|---|---|---|
| Crude IFN-α | 10 | 430% |
| | 50 | 550% |
| | 250 | 480% |
| Control 1 | | 20% |
| Purified IFN-α | 25 | 220% |
| | 125 | 250% |
| | 625 | 600% |
| Control 2 | | 0 |

$^x$Lymphocytes were isolated from buffy coats by sedimentation from ficoll-verografine solution (D = 1,077). Target cells - K562 - cultivated in monolayer in RPMI-1640 with 10% fetal serum, glutamine and antibiotics. Before use the target cells were incubated with 50 μCu Na$^{51}$CrO$_4$ per 7 mln cells. Radioactivity was measured in cultural fluid in a 16 hour cytotoxic test.
Control 1 - medium after cultivation of noninduced cells.
Control 2 - protein fraction purified from placebo by method known for Human Leucocyte Interferon.

TABLE 1

EFFECT OF VARIOUS PROTEIN PREPARATIONS ON IFN-α ACTIVITY$^x$

| Protein components added to medium | The level of Total Protein after Biosynthesis (mg/ml) | Yield activity IFN-α (IU on $1 \times 10^3$ leukocytes) |
|---|---|---|
| Donor plasma (4%) | 3.0 ± 0.3 | 2.67 |
| Plasmal (4%) | 2.4 ± 0.4 | 2.67 |
| Transal (6%) | 0.85 ± 0.13 | 2.67 |

$^x$data from 3 experiments

TABLE 2

ACTIVITY OF PROTEINASES PRESENT IN CRUDE IFN-$^x$

| | | Activity or proteinases$^{xx}$ | |
|---|---|---|---|
| Preparations | Protein (mg/ml) | Extinction at 366 nm | Calculated in % of standard trypsin solution |
| Trypsin Standard 0.025% | — | 0.4 | 100 |
| Plasmal | 2.3 ± 0.4 | 0.11 ± 0.01 | 27 |
| Transal + CPI | 0.67 ± 0.10 | 0 | 0 |

$^x$data of 3 experiments
$^{xx}$activity of proteinases is determined by azacasein test

TABLE 3

THE INFLUENCE OF DIFFERENT IFN PREPARATIONS ON HLA-DR EXPRESSION OF MONONUCLEAR CELLS OF DONOR BLOOD

| Preparations | Concentration (IU/ml) | Index amplification |
|---|---|---|
| IFN-α | 100 | 3.1 ± 1.0 |
| Leukinferon | 100 | 4.4 ± 2.0 |
| IFN-α (recombinant) | 100 | 1.4 ± 0.5 |

TABLE 4

| Leukinferon Conc. | | Day | | | | |
|---|---|---|---|---|---|---|
| | | 3 | 4 | 5 | 6 | 7 |
| 0.5 u/ml | MT4-HIV$^1$ | N.D.$^3$ | — | N.D. | ++ | ++ |
| | MT4$^2$ | N.D. | — | N.D. | — | — |
| 5.0 u/ml | MT4-HIV | N.D. | — | N.D. | — | — |
| | MT4 | N.D. | — | N.D. | — | — |
| 25.0 u/ml | MT4-HIV | — | — | — | — | N.D. |
| | MT4 | — | — | — | — | N.D. |
| 100.0 u/ml | MT4-HIV | — | — | — | — | N.D. |
| | MT4 | — | — | — | — | N.D. |

$^1$MT4 cells incubated with HIV
$^2$MT4 cells alone
$^3$Not Done

TABLE 5

LIST OF CONDITIONS IN WHICH CLINICAL TRIALS HAVE BEEN CONDUCTED USING LEUKINFERON

A. BACTERIAL INFECTIONS:
    Prophylaxis
        Infectious complications after surgery or child birth.
    Therapy
        Purulent-septic infections
        Acute and chronic bronchitis
        Acute and chronic pneumonia
        Legionairres disease
        Pulmonary tuberculosis
        Salmonellosis
        Acute and chronic pyelonephritis
        Peritonitis
        Salpingo-ophoritis

TABLE 5-continued

LIST OF CONDITIONS IN WHICH CLINICAL TRIALS HAVE BEEN CONDUCTED USING LEUKINFERON

B. VIRAL INFECTIONS
  Acute and chronic viral hepatitis
  Influenza and other viral respiratory infections
  Shingles
  Chicken-pox
  Stomatitis
C. ONCOLOGICAL DISEASE
  Basal cell carcinoma
  Breast Cancer

TABLE 6

THE EFFECT OF LEUKINFERON THERAPY ON VARIOUS IMMUNOLOGICAL PARAMETERS IN YOUNG CHILDREN WITH SEPSIS

| Groups | Immunological parameters | | | | | |
|---|---|---|---|---|---|---|
| | IRL (u/ml) | CIC (u/ml) | Spontaneous NCT-test (%) | Phagocytic neutrophilis (%) | Phagocytic index (cell/lymf) | Completeness of phagocytosis (%) |
| Basic therapy | 3.0 ± 0.3 | 221 ± 14 | 8.5 ± 0.9 | 31.4 ± 4.9 | 3.9 ± 0.7 | 38.4 |
| + Leukinferon | 25.2 ± 5.4 | 70 ± 12 | 27.7 ± 6.2 | 62.8 ± 9.2 | 7.2 ± 1.1 | 88.5 |

TABLE 7

STUDY OF VARIOUS IMMUNOLOGICAL PARAMETERS IN PATIENTS WITH SALPINGOOOPHORITE FOLLOWING TREATMENT WITH LEUKINFERON (30 PATIENTS).

| Immunological Parameter | Before therapy | After therapy | Reliability |
|---|---|---|---|
| IgM (g/l) | 1.3 ± 0.1 | 1.3 ± 0.1 | not |
| IgG (g/l) | 8.9 ± 0.5 | 9.4 ± 0.3 | not |
| $T_{total}$ | 624 ± 32 | 938 ± 31 | $p<0.001$ |
| RBTL on PHA | 24.2 ± 1.7 | 29.1 ± 1.7 | $p<0.001$ |
| E-RFC | 23.4 ± 1.8 | 30.0 ± 1.5 | $p<0.001$ |
| $B_{total}$ | 496 ± 38 | 558 ± 20 | not |
| Circulating immune complexes | 3.5 ± 0.3 | 2.6 ± 0.2 | 0.01 |
| $C_3$ (g/l) | 0.98 | 1.0 | not |
| $C_4$ (g/l) | 0.24 | 0.24 | not |

TABLE 8

THE INFLUENCE OF LEUKINFERON OF DYNAMICS OF MONONUCLEAR SUBPOPULATIONS IN PATIENTS WITH BREAST CANCER

| Subpopulation | Antigens of differentiation |
|---|---|
| INCREASED: | |
| T-helpers, NK and other cytotoxic subpopulations | (CD4, CD11a, CD11b, CD38) |
| The level of activated mononuclears, expressing MHC antigens | (HLA-A,B,C, HLA-DR) |
| WITHOUT CHANGES OR DECREASED: | |
| T-supressors | (CD8, CD58, CD22) |
| DECREASED: | |
| The level of monocyte-myeloid cells | (CD15) |

I claim:

1. A method of producing a transal composition containing transferrin, albumin and a 40 kDa protein, said method comprising the steps of:
  a) mixing plasma with chloroform;
  b) recovering a first aqueous phase from the plasma/chloroform mixture of step a) and adjusting the pH of the first aqueous phase to 8.5;
  c) precipitating gamma globulins from the first aqueous phase with polyethylene glycol;
  d) recovering a second aqueous phase from step c);
  e) passing the second aqueous phase through an anion exchange column equilibrated with 0.01M tris-HCl buffer, pH 8.5 and 0.01M NaCl; and
  f) recovering proteins that bind to the column by passing a solution of 0.01M tris-HCl buffer, pH 8.5 and 0.5M NaCl through the column, wherein the proteins eluted in step f) consist of the transal composition.

2. A transal composition prepared according to the method of claim 1.

3. A transal composition isolated from plasma consisting essentially of transferrin, albumin and a 40 kDa protein.

4. A method of producing a complex of proteinase inhibitors composition containing $\alpha_2$-macroglobulin, a 160 kDa protein, an 80–60 kDa protein and a 20 kDa protein, said method comprising the steps of:
  a) mixing plasma with chloroform;
  b) recovering a first aqueous phase from the plasma/chloroform mixture of step a) and adjusting the pH of the first aqueous phase to 8.5;
  c) precipitating gamma globulins from the first aqueous phase with polyethylene glycol;
  d) recovering a second aqueous phase from step c);
  e) passing the second aqueous phase through an anion exchange column equilibrated with 0.01M tris-HCl buffer, pH 8.5 and 0.01M NaCl;
  f) collecting an eluate that passes freely through the column and adjusting the pH of said eluate to pH 6.5;
  g) passing said eluate through a $Cu^{++}$ chelate anion-exchange column equilibrated with 0.02M phosphate buffer, pH 6.5 and 0.8M NaCl; and
  h) recovering proteins that bind to the column by eluting said column with 0.1M acetate buffer, pH 4.5 and 0.5M NaCl wherein the proteins eluted in step h) consist of the complex of proteinase inhibitors composition.

5. A complex of proteinase inhibitors composition prepared according to claim 4.

6. A complex of proteinase inhibitors composition isolated from plasma consisting essentially of $\alpha_2$macroglobulin, a 160 kDa protein, an 80–60 kDa protein and a 20 kDa protein.

7. A method for producing a cytokine composition comprising the steps of:
   a) culturing leucocytes previously incubated with a virus in a liquid medium containing a transal composition isolated form plasma consisting essentially of transferrin, albumin and a 40 kDa protein and a complex of proteinase inhibitors composition isolated from plasma consisting essentially of $\alpha_2$-macroglobulin, a 160 kDa protein, an 80–60 kDa protein and a 20 kDa protein,
   b) separating the liquid medium from the leucocytes;
   c) removing impurities from the liquid medium; and
   d) recovering from the liquid medium of c) a cytokine composition comprising said transal composition and said complex of proteinase inhibitors composition.

8. The method according to claim 7 wherein in step (a) the transal composition is added at a final concentration of 6% v/v and the complex of proteinase inhibitors composition is added at a final concentration of 15 mg/ml.

9. The method according to claim 8 wherein step a) is carried out for approximately 10–14 hours at approximately 37.5° C.

10. The method according to claim 7 wherein in step (b) the leucocytes are removed by centrifugation.

11. The method according to claim 7 wherein the impurities comprise human virus, foreign antigens, and antibiotics.

12. The method according to claim 11 wherein,
   a) the human virus is removed by chemical inactivation with hydrogen peroxide and chloroform;
   b) the antibiotics are removed by gel filtration; and
   c) the foreign antigens are removed by negative immunoabsorption on a column containing antibodies specific for the antigens.

13. A method for producing a cytokine composition comprising the steps of:
   a) culturing leucocytes previously incubated with a virus in a liquid culture medium containing a transal composition isolated form plasma consisting essentially of transferrin, albumin and a 40 kDa protein and a complex of proteinase inhibitors composition isolated from plasma consisting essentially of $\alpha_2$-macroglobulin, a 160 kDa protein, an 80–60 kDa protein and a 20 kDa protein;
   b) removing the leucocytes from the liquid medium;
   c) treating the liquid medium to remove impurities; and
   d) recovering a cytokine composition comprising said transal composition and said complex of proteinase inhibitors composition;
   said transal composition being prepared by a method comprising the steps of:
   a) mixing plasma with chloroform;
   b) recovering a first aqueous phase from the plasma/chloroform mixture of step a) and adjusting the pH of the first aqueous phase to 8.5;
   c) precipitating gamma globulins from the first aqueous phase with polyethylene glycol;
   d) recovering a second aqueous phase from step c);
   e) passing the second aqueous phase through an anion exchange column equilibrated with 0.01M tris-HCl buffer, pH 8.5 and 0.01M NaCl; and
   f) recovering proteins that bind to the column by passing a solution of 0.01M tris-HCl buffer, pH 8.5 and 0.5M NaCl through the column, wherein the proteins eluted in step f) consist of the transal composition; and
   said complex of protease inhibitors composition being prepared by a method comprising the steps of:
   a) mixing plasma with chloroform;
   b) recovering a first aqueous phase from the plasma/chloroform mixture of step a) and adjusting the pH of the first aqueous phase to 8.5;
   c) precipitating gamma globulins from the first aqueous phase with polyethylene glycol;
   d) recovering a second aqueous phase from step c);
   e) passing the second aqueous phase through an anion exchange column equilibrated with 0.01M tris-HCl buffer, pH 8.5 and 0.01M NaCl;
   f) collecting an eluate that passes freely through the column and adjusting the pH of said eluate to pH 6.5;
   g) passing said eluate through a $Cu^{++}$ chelate anion exchange column equilibrated with 0.02M phosphate buffer, pH 6.5 and 0.8M NaCl; and
   h) recovering proteins that bind to the column by eluting said column with 0.1M acetate buffer, pH 4.5 and 0.5M NaCl wherein the proteins eluted in step h) consist of the complex of proteinase inhibitors composition.

14. A cytokine composition prepared according to the method of claim 13.

15. The cytokine composition of claim 14 further comprising a diluent or carrier.

16. A method of enhancing the effectiveness of the immune system comprising administering to a person in need of such treatment in an amount effective for said treatment a cytokine composition prepared according to claim 7.

17. The method of claim 16 wherein the person treated has a viral infection.

18. The method of claim 16 wherein the person treated has a bacterial infection.

* * * * *